US00PP22242P2

(12) United States Plant Patent
Robb

(10) Patent No.: US PP22,242 P2
(45) Date of Patent: Nov. 8, 2011

(54) ***LYSIMACHIA* PLANT NAMED 'MIDNIGHT SUN'**

(50) Latin Name: *Lysimachia congestiflora*
Varietal Denomination: Midnight Sun

(76) Inventor: John Robb, Kariong (AU)

( * ) Notice: Subject to any disclaimer, the term of this patent is extended or adjusted under 35 U.S.C. 154(b) by 7 days.

(21) Appl. No.: 12/799,851

(22) Filed: May 4, 2010

(51) Int. Cl.
*A01H 5/00* (2006.01)

(52) U.S. Cl. ..... Plt./453

(58) Field of Classification Search ..... Plt./263.1, Plt./453
See application file for complete search history.

*Primary Examiner* — Susan McCormick Ewoldt
(74) *Attorney, Agent, or Firm* — C. A. Whealy

(57) ABSTRACT

A new and distinct cultivar of *Lysimachia* plant named 'Midnight Sun', characterized by its compact and prostrate to trailing growth habit; freely branching habit; freely flowering habit; long flowering period; relatively large yellow-colored flowers; and good garden performance.

2 Drawing Sheets

Botanical designation: *Lysimachia congestiflora.*
Cultivar denomination: 'MIDNIGHT SUN'.

BACKGROUND OF THE INVENTION

The present invention relates to a new and distinct cultivar of *Lysimachia* plant, botanically known as *Lysimachia congestiflora* and hereinafter referred to by the name 'Midnight Sun'.

The new *Lysimachia* plant is a product of a planned breeding program conducted by the Inventor in Kulnurra, New South Wales, Australia. The objective of the breeding program is to create new compact *Lysimachia* plants with numerous large flowers and good garden performance.

The new *Lysimachia* plant originated from an open-pollination during the spring of 2003 in Kulnurra, New South Wales, Australia of an unnamed selection of *Lysimachia congestiflora*, not patented, as the female, or seed, parent with an unknown selection of *Lysimachia congestiflora* as the male, or pollen, parent. The new *Lysimachia* plant was discovered and selected by the Inventor as a single flowering plant within the progeny of the stated open-pollination in a controlled greenhouse environment in Kulnurra, New South Wales, Australia during the spring of 2004.

Asexual reproduction of the new *Lysimachia* plant by cuttings in a controlled greenhouse environment in Kulnurra, New South Wales, Australia since 2005, has shown that the unique features of this new *Lysimachia* plant are stable and reproduced true to type in successive generations.

SUMMARY OF THE INVENTION

Plants of the new *Lysimachia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Midnight Sun'. These characteristics in combination distinguish 'Midnight Sun' as a new and distinct cultivar of *Lysimachia* plant:

1. Compact and prostrate to trailing growth habit.
2. Freely branching habit.
3. Freely flowering habit; long flowering period.
4. Relatively large yellow-colored flowers.
5. Good garden performance.

Plants of the new *Lysimachia* can be compared to plants of the female parent selection. Plants of the new *Lysimachia* differ from plants of the female parent selection in the following characteristics:

1. Plants of the new *Lysimachia* are more compact than plants of the female parent selection.
2. Stems of plants of the new *Lysimachia* are darker greyed purple in color than stems of plants of the female parent selection.
3. Flowers of plants of the new *Lysimachia* are slightly darker yellow in color than flowers of plants of the female parent selection.

Plants of the new *Lysimachia* can be compared to plants of the *Lysimachia congestiflora* 'Outback Sunset', disclosed in U.S. Plant patent application Ser. No. 08/726,423, now abandoned. In side-by-side comparisons conducted in Cranbourne, Victoria, Australia, plants of the new *Lysimachia* differed from plants of 'Outback Sunset' in the following characteristics:

1. Plants of the new *Lysimachia* were shorter, broader and more prostrate than plants of 'Outback Sunset'.
2. Stems of plants of the new *Lysimachia* were greyed purple in color whereas stems of plants of 'Outback Sunset' were yellow in color.
3. Plants of the new *Lysimachia* had smaller leaves than plants of 'Outback Sunset'.
4. Leaves of plants of the new *Lysimachia* were green in color with greyed purple-colored blotches whereas leaves of 'Outback Sunset' were green and yellow green variegated.

BRIEF DESCRIPTION OF THE PHOTOGRAPHS

The accompanying colored photographs illustrate the overall appearance of the new *Lysimachia* plant showing the colors as true as it is reasonably possible to obtain in colored reproductions of this type. Colors in the photographs may differ slightly from the color values cited in the detailed botanical description which accurately describe the colors of the new *Lysimachia* plant.

The photograph on the first sheet comprises a top perspective view of typical flowering plants of 'Midnight Sun' grown in containers.

The photograph on the second sheet is a close-up view of a typical flowering plant of 'Midnight Sun'.

DETAILED BOTANICAL DESCRIPTION

The aforementioned photographs and following observations, measurements and values describe plants grown during the spring in 15-cm containers in a polyethylene-covered greenhouse in Cranbourne, Victoria, Australia and under cultural conditions which approximate commercial *Lysimachia* plant production. During the production of the plants, day temperatures ranged from 10° C. to 40° C., night temperatures ranged from 4° C. to 28° C. and light levels ranged from 5,000 to 9,000 foot-candles. Rooted young plants were pinched one time and were four months old when the photographs and description were taken. In the following description, color references are made to The Royal Horticultural Society Colour Chart, 1995 Edition, except where general terms of ordinary dictionary significance are used.

Botanical classification: *Lysimachia congestiflora* 'Midnight Sun'.

Parentage:

- *Female, or seed, parent.*—Unnamed selection of *Lysimachia congestiflora*, not patented.
- *Male, or pollen, parent.*—Unknown selection of *Lysimachia congestiflora*, not patented.

Propagation:

- *Type.*—By cuttings.
- *Time to initiate roots, summer.*—About 10 to 20 days at 22° C. to 30° C.
- *Time to initiate roots, winter.*—About 16 to 30 days at 10° C. to 15° C.
- *Time to produce a rooted young plant, summer.*—About 20 to 30 days at 16° C. to 39° C.
- *Time to produce a rooted young plant, winter.*—About 25 to 45 days at 10° C. to 15° C.
- *Root description.*—Fine, fibrous; white to brown in color.
- *Rooting habit.*—Freely branching; dense.

Plant description:

- *Plant and growth habit.*—Herbaceous annual; compact and prostrate to trailing growth habit; freely branching habit; vigorous growth habit.
- *Plant height.*—About 5 cm to 10 cm.
- *Plant diameter.*—About 60 cm to 100 cm.

Lateral branch description:

- *Length.*—About 20 cm to 30 cm.
- *Diameter.*—About 2 mm to 3 mm.
- *Internode length.*—About 1 cm to 5 cm.
- *Aspect.*—About 90° from vertical.
- *Texture.*—Sparsely pubescent.
- *Color.*—Close to 183A to 183C.

Foliage description:

- *Arrangement.*—Opposite, simple.
- *Length.*—About 2 cm to 3.8 cm.
- *Width.*—About 1 mm to 2 cm.
- *Shape.*—Broadly ovate.
- *Apex.*—Bluntly acute.
- *Base.*—Blunt.
- *Margin.*—Entire.
- *Texture, upper and lower surfaces.*—Sparsely pubescent.
- *Venation pattern.*—Palmate.
- *Color.*—Developing leaves, upper surface: Close to 146B; blotches, close to 200A. Developing leaves, lower surface: Close to 196C and 187A. Fully expanded leaves, upper surface: Close to 146A to 146B; blotches, close to 187A; venation, close to 147A to 147B. Fully expanded leaves, lower surface: Close to 187A; venation, close to 195A.
- *Petiole length.*—About 2 mm to 4 mm.
- *Petiole diameter.*—About 1 mm.
- *Petiole texture, upper and lower surfaces.*—Pubescent.
- *Petiole color, upper surface.*—Close to 63D.
- *Petiole color, lower surface.*—Close to 63B to 63C.

Flower description:

- *Flower arrangement and habit.*—Campanulate flowers with flaring petals; flowers arranged on terminal umbels; freely flowering habit with about two to seven open flowers per umbel; flowers face upright.
- *Fragrance.*—None detected.
- *Natural flowering season.*—Plants flower continuously from the spring through the fall in Victoria, Australia; plants begin flowering about eight to twelve weeks after planting.
- *Flower longevity.*—Individual flowers last about 10 to 14 days on the plant; flowers not persistent.
- *Inflorescence height.*—About 1.5 cm.
- *Inflorescence diameter.*—About 2.5 cm to 3 cm.
- *Flower diameter.*—About 1.4 cm to 2.1 cm.
- *Flower length.*—About 1.3 cm to 1.5 cm.
- *Flower bud.*—Shape: Cone-shaped. Length: About 9 mm to 12 mm. Diameter: About 4 mm. Color: Between 9A and 12A.
- *Petals.*—Arrangement: Five petals arranged in a single whorl. Length: About 1.3 cm to 1.5 cm. Width: About 5 mm to 6 mm. Shape: Elliptic to broadly lanceolate. Apex: Acute, slightly reflexed. Base: Attenuate. Margin: Entire. Texture, upper and lower surfaces: Smooth, glabrous. Color: When opening, upper and lower surfaces: Close to 12A. Fully opened, upper and lower surfaces: Close to 12A; with development, color becoming closer to 13B.
- *Sepals.*—Arrangement: Five sepals fused in a single whorl. Length: About 7 mm to 8 mm. Width: About 2 mm. Shape: Narrowly lanceolate. Apex: Acute. Base: Obtuse. Margin: Entire. Texture, upper surface: Smooth, glabrous. Texture, lower surface: Pubescent. Color, upper surface: Close to 156C to 156D; towards the apex, close to 199B. Color, lower surface: Close to 161B to 161C; towards the apex, close to 177A.
- *Peduncles.*—Length: About 6 cm to 10 cm. Diameter: About 1 mm to 2 mm. Angle: Mostly erect. Texture: Densely pubescent. Color: Close to 183C; towards the apex, close to 193A.
- *Pedicels.*—Length: About 4 mm to 6 mm. Diameter: About 1 mm. Angle: Ascending to erect. Texture: Sparsely pubescent. Color: Close to 193A.
- *Reproductive organs.*—Stamens: Quantity per flower: About five to six. Filament length: About 3 mm to 5 mm. Filament color: Close to 12C. Anther length: About 1 mm. Anther shape: Narrowly deltoid. Anther color: Close to 12B. Pollen amount: Moderate. Pollen color: Close to 12B. Pistils: Quantity: One per flower.

Pistil length: About 5 mm. Style length: About 6 mm Style color: Close to 4C. Stigma color: Close to 7A.

*Seeds.*—Seed development has not been observed on plants of the new *Lysimachia.*

Garden performance: Plants of the new *Lysimachia* have been observed to have good garden performance and tolerate wind, rain and to tolerate temperatures ranging from −2° C. to 44° C.

Pathogen/pest resistance: Plants of the new *Lysimachia* have not been observed to be resistant to pathogens and pests common to *Lysimachia* plants.

It is claimed:

1. A new and distinct *Lysimachia* plant named 'Midnight Sun' as illustrated and described.

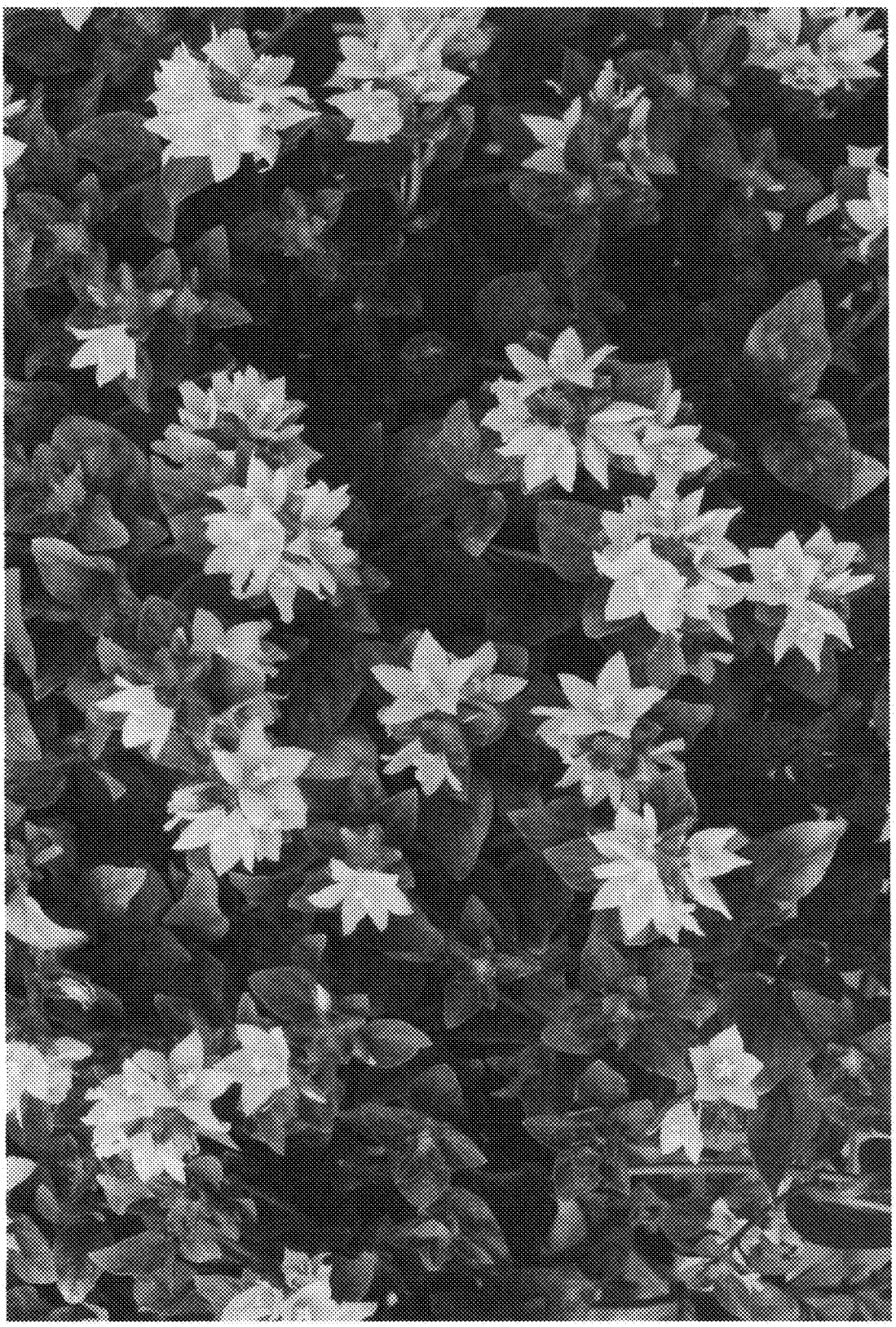

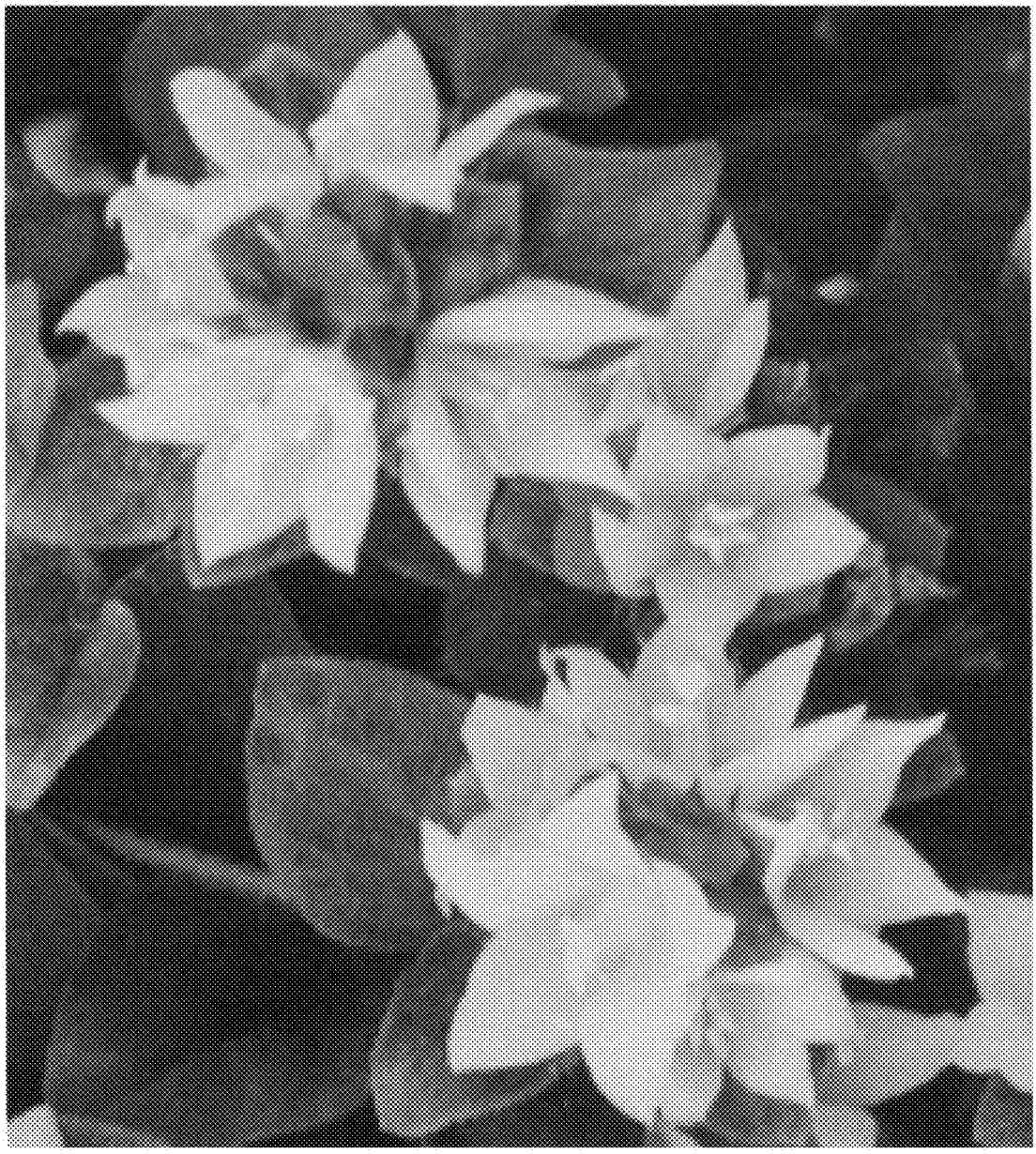

* * * * *